US00PP28870P3

(12) United States Plant Patent
Randag

(10) Patent No.: US PP28,870 P3
(45) Date of Patent: Jan. 9, 2018

(54) VARIETY OF CALLA LILY PLANT NAMED 'MONTEVIDEO'

(50) Latin Name: *Zantedeschia sprengeri*
Varietal Denomination: Montevideo

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 59 days.

(21) Appl. No.: 14/998,461

(22) Filed: Jan. 6, 2016

(65) Prior Publication Data

US 2016/0212922 P1 Jul. 21, 2016

Related U.S. Application Data

(60) Provisional application No. 62/125,226, filed on Jan. 15, 2015.

(51) Int. Cl.
*A01H 5/02* (2006.01)

(52) U.S. Cl.
USPC ..... Plt./490

(58) Field of Classification Search
USPC ..... Plt./490
CPC ..... A01H 5/0272
See application file for complete search history.

*Primary Examiner* — Kent L Bell
(74) *Attorney, Agent, or Firm* — The Webb Law Firm

(57) ABSTRACT

'Montevideo' is a new variety of calla lily plant having inflorescences with a dark purple-colored spathe that produces 3-22 inflorescences per tuber. The height of the top of an inflorescence above the soil can reach up to 50 cm, and the leaves are dark green with transparent maculations present and have a leathery texture. Further, the leaves have a dark purple-colored margin.

2 Drawing Sheets

CROSS REFERENCE TO RELATED APPLICATION

This application claims the benefit of U.S. Provisional Patent Application Ser. No. 62/125,226, having a filing date of Jan. 15, 2015, and entitled "Varieties of Calla Lily Plants", the entire disclosure of which is incorporated herein by reference.

Botanical classification: *Zantedeschia sprengeri.*
Varietal denomination: 'MONTEVIDEO'.

BACKGROUND OF THE NEW PLANT

The present invention comprises a new and distinct cultivar of calla lily, botanically known as *Zantedeschia sprengeri* and hereinafter referred to by the cultivar name 'Montevideo'.

'Montevideo' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as C04020 (female parent, unpatented) with *Zantedeschia sprengeri* 'Black Star' (male parent, U.S. Plant Pat. No. 14,844). 'Montevideo' was selected in 2007 by the inventor in 't Zand, The Netherlands as one flowering plant within the progeny of the stated cross.

The first act of asexual reproduction of 'Montevideo' by tissue culture was performed by the inventor in September of 2010 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 14 cm pots in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Montevideo' which, in combination, distinguish this calla lily as a new and distinct cultivar:

1. Dark purple-colored spathe and leaf margin;
2. Inflorescences above the leaf canopy; and
3. High inflorescence production.

Further, when compared to calla lily plant names 'Schwarzwalder' (U.S. Plant Pat. No. 11,001), 'Schwarzwalder' has an upper surface spathe color of Greyed-Purple Group RHS 187A and a lower surface spathe color that varies between Greyed-Purple Group RHS 187A and Black Group RHS 202A, whereas 'Montevideo' has an upper and lower surface spathe color that varies between Greyed-Purple Group RHS 186A and 186B.

Table 1 provides similarities and differences of 'Montevideo' to its parents, *Zantedeschia sprengeri* selection C04020 and *Zantedeschia sprengeri* 'Black Star'.

TABLE 1

| 'Montevideo' | Similarities | Differences |
|---|---|---|
| C04020 | Number of inflorescences<br>Spathe shape | Spathe color<br>White leaf spots<br>Leaf shape |
| 'Black Star' | Leaf shape<br>Spathe color<br>Leaf margin | Spathe color<br>Number of inflorescences<br>Spathe shape |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
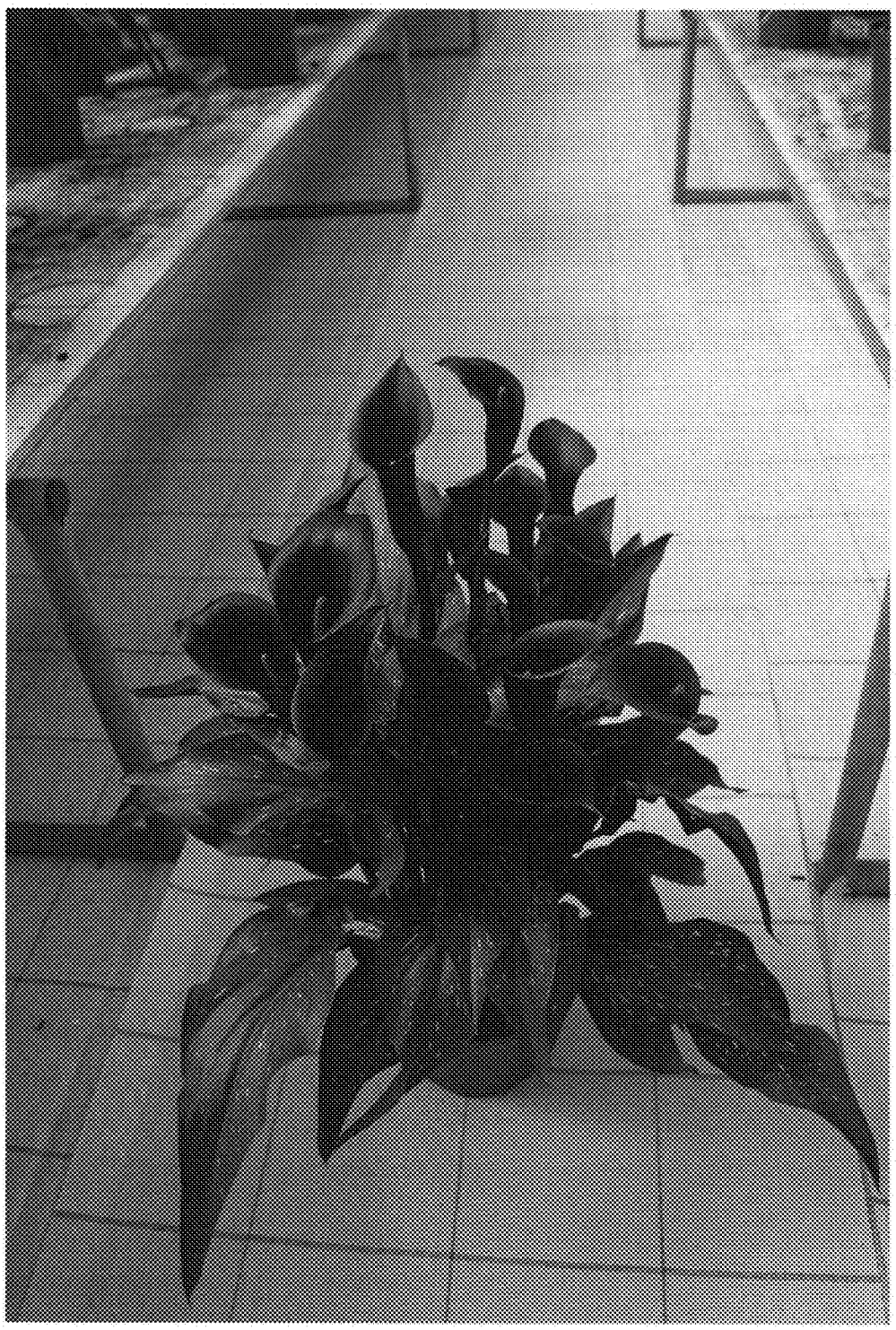
FIG. 1 is a photograph of a plant of the new variety.
Figure 2:
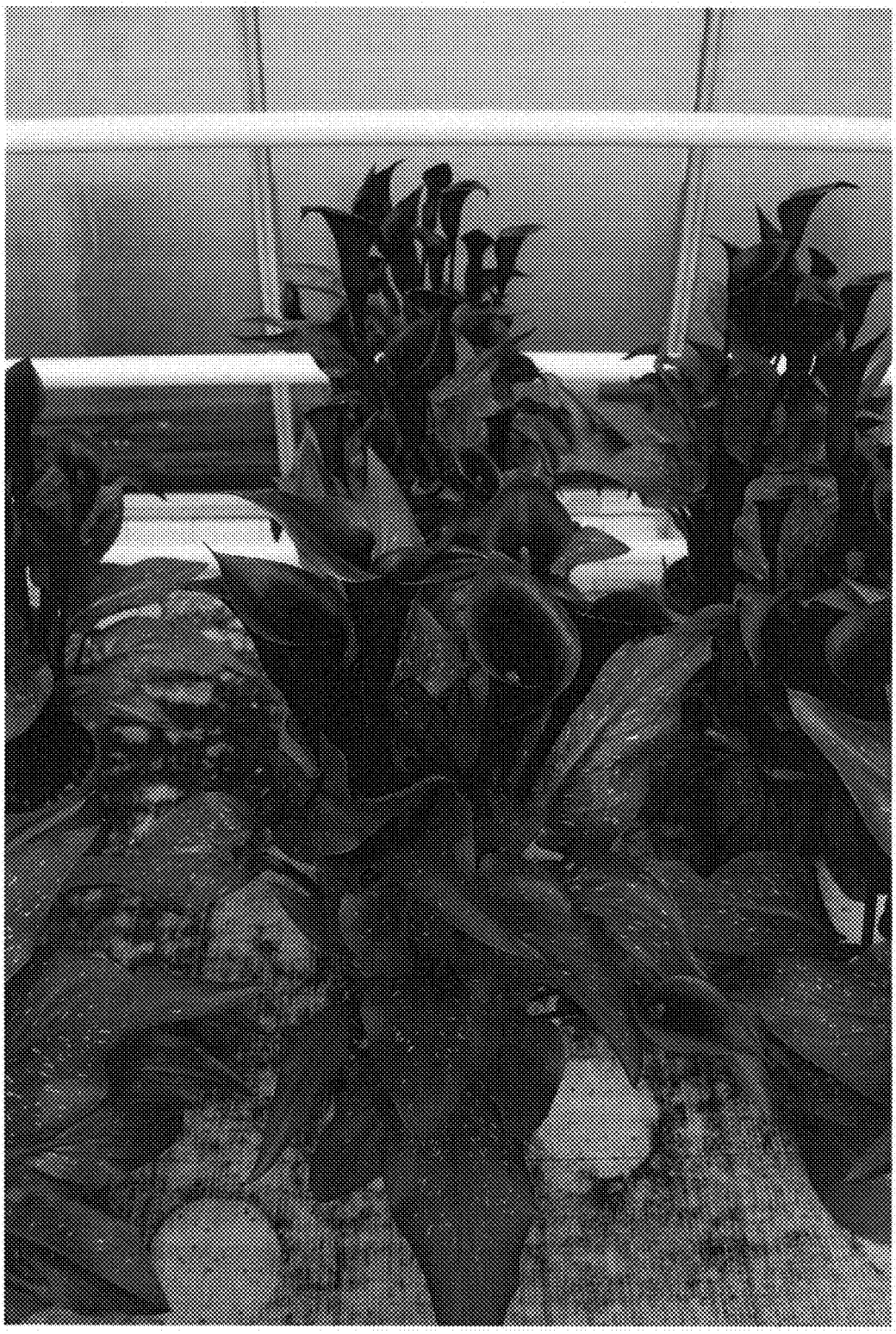
FIG. 2 is a photograph of a group of multiple plants of the new variety.

Size:

*Height of the leaf canopy above the soil.*—5-45 cm.

*Height of top of inflorescence above the soil.*—10-50 cm.

*Diameter.*—20-60 cm.

Form: Erect.

Number of inflorescences per tuber:

*Size* 14-16 *cm in diameter.*—3-7 inflorescences.

*Size* 16-18 *cm in diameter.*—5-15 inflorescences.

*Size* 18-20 *cm in diameter.*—8-22 inflorescences.

Branches:

*Character.*—Many; like the variety 'Odessa' (U.S. Plant Pat. No. 18,833).

*Color.*—Between Greyed-Purple Group RHS N186C and N186D.

Leaves:

*Size.*—Width: 4-11 cm. Length: 8-23 cm.

*Number per plant.*—20-40.

*Shape.*—Lanceolate.

*Color.*—Upper surface: Green Group RHS 137A to 137B, having transparent maculations between White Group RHS 155B and N155A. Lower surface: Green Group RHS 137A to 137B, having transparent maculations between White Group RHS 155B and N155A.

*Apex.*—Acuminate.

*Base.*—Obtuse/truncate.

*Margin.*—Undulate; having a color of Greyed-Purple Group RHS 187A to 187B.

*Veins.*—Configuration: Pinnate. Color: Upper Surface: Green Group RHS 137A to Yellow-Green Group 144A. Lower Surface: Green Group RHS 137A to Yellow-Green Group N144A.

*Surface quality.*—Leathery.

*Petiole.*—Length: 5-25 cm. Diameter: 7 mm. Color: The base is between White Group RHS 155A and Greyed-Purple Group RHS 186D, and the upper part is between Greyed-Purple Group RHS 187A to 187B.

Roots:

*Color.*—White.

*Branching.*—Similar to other *Zantedeschia* varieties.

The Inflorescence and Seeds

Spathe:

*Size.*—Length (measured from opening to tip): 3-8 cm. Width: 3-5.5 cm. Height: 3-12 cm.

*Color.*—Upper surface: Varies between Greyed-Purple Group RHS 186A and 186B. Lower surface: Varies between Greyed-Purple Group RHS 186A and 186B.

*Vein color.*—Between Greyed-Purple Group RHS 186A and 186B.

*Shape.*—Cupped.

*Apex.*—Apiculate.

*Margin.*—Entire.

Spadix:

*Size.*—Length: 17-55 mm. Diameter: 3-10 mm.

*Color.*—Between Greyed-Purple Group RHS 183A and N186B.

*Position relative to spathe.*—Upright.

Peduncle:

*Size.*—Length: 10-45 cm. Diameter: 3-11 mm.

*Color.*—The upper part is between Greyed-Purple Group RHS N186C and 187A, and the lower part is between Green-White Group RHS 157C and Greyed-Purple Group RHS 186D.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Similar to 'Picasso' (U.S. Plant Pat. No. 15,282). Color: Between White Group RHS 155A and 155B.

*Anther.*—Shape: Round. Length: Less than 1 mm. Color: Between Greyed-Purple Group RHS 183A and N186B.

*Filament.*—Length: Less than 1 mm. Color: Between White Group RHS 155A and 155B.

*Pistils.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 8A and 8B.

*Ovaries.*—Texture: Smooth. Length: Between 1 to 10 mm. Width: Between 1 to 10 mm. Color: Top color is between Purple Group RHS N79A and N79B, bottom color is from White Group RHS 155B to Green-White Group RHS 157C.

Seeds:

*Length.*—4-7 mm.

*Width.*—3-6 mm.

*Color.*—Between Purple Group RHS N79B and N79D.

*Amount.*—Between 1-55.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July.

Lastingness: About two weeks on the plant.

Fragrance: None.

I claim:

1. A new and distinct variety of calla lily plant named 'Montevideo' as herein described and illustrated.

* * * * *